US010501783B2

(12) United States Patent
Fang et al.

(10) Patent No.: US 10,501,783 B2
(45) Date of Patent: Dec. 10, 2019

(54) NUCLEIC ACID DETECTION AND QUANTIFICATION

(71) Applicant: QIAGEN GMBH, Hilden (DE)

(72) Inventors: Nan Fang, Hilden (DE); Andreas Missel, Hilden (DE); Katja Heitz, Hilden (DE); Holger Wedler, Hilden (DE)

(73) Assignee: QIAGEN GMBH, Hilden (DE)

( * ) Notice: Subject to any disclaimer, the term of this patent is extended or adjusted under 35 U.S.C. 154(b) by 295 days.

(21) Appl. No.: 15/102,685

(22) PCT Filed: Dec. 9, 2014

(86) PCT No.: PCT/EP2014/077064
§ 371 (c)(1),
(2) Date: Jun. 8, 2016

(87) PCT Pub. No.: WO2015/086604
PCT Pub. Date: Jun. 18, 2015

(65) Prior Publication Data
US 2016/0298182 A1 Oct. 13, 2016

(30) Foreign Application Priority Data

Dec. 11, 2013 (EP) ..................................... 13196721

(51) Int. Cl.
*C12P 19/34* (2006.01)
*C12Q 1/6851* (2018.01)
*C12Q 1/6818* (2018.01)
*C12Q 1/686* (2018.01)

(52) U.S. Cl.
CPC ........... *C12Q 1/6851* (2013.01); *C12Q 1/686* (2013.01); *C12Q 1/6818* (2013.01)

(58) Field of Classification Search
CPC ........ C12Q 2561/113; C12Q 2563/173; C12Q 2565/1025; C12Q 1/6818; C12Q 1/6851; C12Q 1/686; C12Q 2563/107
USPC ........................................................ 435/91.2
See application file for complete search history.

(56) References Cited

U.S. PATENT DOCUMENTS

2016/0222427 A1* 8/2016 So ........................ C12Q 1/6886

FOREIGN PATENT DOCUMENTS

| EP | 3080291 A1 | 10/2016 |
| WO | WO-2006/044994 A2 | 4/2006 |
| WO | WO-2011/143478 A2 | 11/2011 |
| WO | WO-2015/086604 A1 | 6/2015 |

OTHER PUBLICATIONS

Iluumina, Paired-End Sequencing Sample Preparation Guide, pp. 1-34 (Year: 2009).*
EP, 14809053.3 (3080291), Dec. 9, 2014 (Oct. 19, 2016), Fang et al. (Qiagen GmbH).
PCT, PCT/EP2014/077064 (WO 2015/086604), Dec. 9, 2014 (Jun. 18, 2015), Fang et al. (Qiagen GmbH).
Gudnason, H. et al., Comparison of Multiple DNA Dyes for Real-Time PCR: Effects of Dye Concentration and Sequence Composition on DNA Amplification and Melting Temperature. Nucleic Acid Res. 2007; 35(19):e127.
Kolesar, J.M. et al., Direct Quantification of HIV-1 RNA by Capillary Electrophoresis with Laser-Induced Fluorescence. J Chromatography B. 1997; 697:189-94.
Lind, K. et al., Combining Sequence-Specific Probes and DNA Binding Dyes in Real-Time PCR for Specific Nucleic Acid Quantification and Melting Curve Analysis. Biotechniques. 2006; 40(3):315-9.
Sun, Z. et al., Multiplex Locked Nucleic Acid Probes for Analysis of Hepatitis B Virus Mutants Using Real-Time PCR. Genomics. 2007; 89:151-9.
Communication Pursuant to 94(3) EPC dated Jul. 5, 2017 by the European Patent Office for Application No. 14809053.3, which was filed on Dec. 9, 2014 and published as EP 3080291 on Oct. 19, 2016 (Inventor—Fang et al.; Applicant—Qiagen GmbH) (7 pages).
International Search Report and Written Opinion dated Feb. 23, 2015 by the International Searching Authority for Patent Application No. PCT/EP2014/077064, which was filed on Dec. 9, 2014 and published as WO 2015/086604 (Inventor—Fang et al.; Applicant—Qiagen GmbH) (11 pages).
International Preliminary Report on Patentability dated Jun. 14, 2016 by the International Searching Authority for Patent Application No. PCT/EP2014/077064, which was filed on Dec. 9, 2014 and published as WO 2015/086604 (Inventor—Fang et al.; Applicant—Qiagen GmbH) (7 pages).
Anonymous: "Paired-End Sequencing Sample Preparation Guide", (2009), pp. 1-34, Retrieved from the Internet: URL: http://mmijggl.caltech.edw/sequencing/PairedEnd_SamplePrep_Guide_1005063_B.pdf [retrieved on Feb. 1, 2019].
Gansauge, Marie-Theres, et al.: "Single-stranded DNA library preparation for the sequencing of ancient or damaged DNA", Nature Protocols, vol. 8, No. 4, Mar. 14, 2013, pp. 737-748.

(Continued)

*Primary Examiner* — Cynthia B Wilder
(74) *Attorney, Agent, or Firm* — Ballard Spahr LLP

(57) ABSTRACT

The present invention relates to methods and uses for the detection or quantification of newly-synthesized double-stranded target nucleic acid molecules in a sample during quantitative real-time polymerase chain reaction (qPCR) amplification. According to the invention, an intercalating dye recognizing double-stranded DNA molecules with higher affinity than single-stranded DNA molecules and a fluorophore-labeled oligonucleotide-probe being sequence specific for a target nucleic acid molecule are simultaneously employed, thus enabling quantification a specific target and total amount of a mixed nucleic acid population, and enabling assessing the cause of suboptimal PCR performance.

Figure 1A:
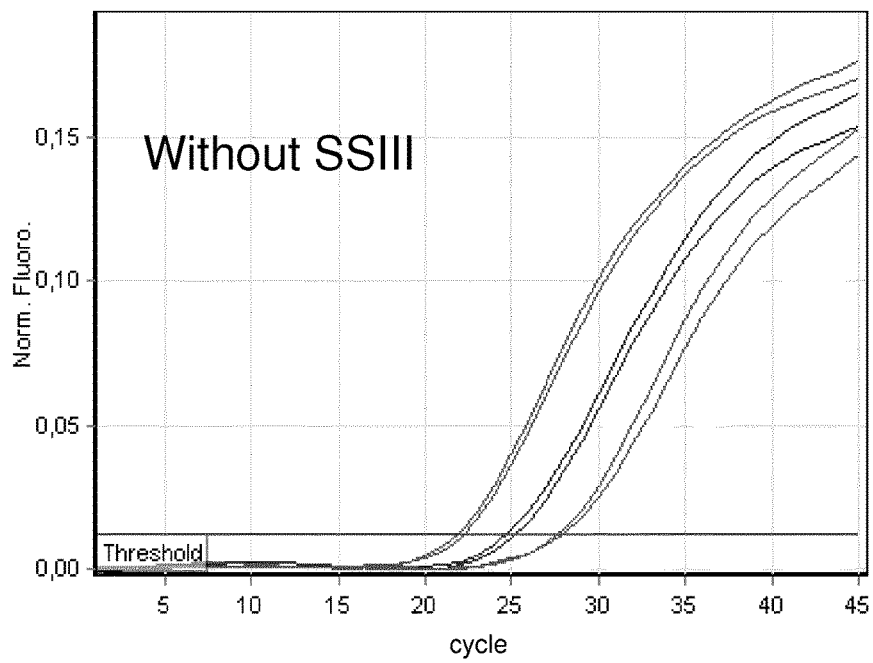

6 Claims, 10 Drawing Sheets
Specification includes a Sequence Listing.

(56) References Cited

OTHER PUBLICATIONS

Meyer, M., et al.: "Illumina Sequencing Library Preparation for Highly Multiplexed Target Capture and Sequencing", Cold Spring Harbor Protocols, vol. 2010, No. 6, (2010), pp. 1-10.
Communication pursuantto Article 94(3) EPC dated Feb. 7, 2019 by the European Patent Office for EP Application No. 14809053.3, filed on Dec. 9, 2014 and published as EP 3080291 A1 on Oct. 19, 2016 (Applicant-Qiagen GmbH) (9 Pages).

* cited by examiner

| Template Amount | Ct (Mean) No SSIII |
|---|---|
| 10ng | 22.06 |
| 1ng | 25.05 |
| 0.1ng | 27.81 |

Fig. 1C

| Template Amount | Ct (Mean) With SSIII |
|---|---|
| 10ng | 27.16 |
| 1ng | 30.28 |
| 0.1ng | 33.80 |

Fig. 1D

| Template Amount | Ct (Mean) |
|---|---|
| 10ng | 17,03 |
| 1ng | 20,01 |
| 0.1ng | 22,95 |

Fig. 2C

| Template Amount | Ct (Mean) |
|---|---|
| 10ng | 23.26 |
| 1ng | 24.77 |
| 0.1ng | 25.98 |

Fig. 2D

| Template Amount | Ct Mean SybrGreen | Ct Mean Hex |
|---|---|---|
| 10ng | 17.95 | 23.14 |
| 1ng | 21.22 | 26.31 |
| 0.1ng | 24.71 | 29.62 |

Fig. 4C

| Ratio X adaptor: B Adatpt | Library Concentration as determined by Sybr Green qPCR (nM) | Library Concentration as determined by TaqMan qPCR (Hex) (nM) | Percentage of Effective Library |
|---|---|---|---|
| 1:1 | 578 | 273 | 47,23% |
| 1:3 | 737 | 513 | 69,61% |

Fig. 6B

SEQUENCE LISTING

<160> NUMBER OF SEQ ID NOS: 8

<210> SEQ ID NO 1
<211> LENGTH: 17
<212> TYPE: DNA
<213> ORGANISM: Artificial Sequence
<220> FEATURE:
<223> OTHER INFORMATION: Primer

<400> SEQUENCE: 1
ttccacccat ggcaaat                                                    17

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
gaagatggtg atgggatttc                                                 20

<210> SEQ ID NO 3
<211> LENGTH: 20
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (1)..(1)
<223> OTHER INFORMATION: Hexachloro-fluorescein on 5' end
<220> FEATURE:
<221> NAME/KEY: misc_feature
<222> LOCATION: (20)..(20)
<223> OTHER INFORMATION: Black Hole quencher on 3' end

<400> SEQUENCE: 3
caagcttccc gttctcagcc                                                 20

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
gccgctagag gtgaaattct tg                                              22

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
cattcttggc aaatgctttc g                                               21

<210> SEQ ID NO 6
<211> LENGTH: 25
<212> TYPE: DNA
<213> ORGANISM: Artificial Sequence
<220> FEATURE:
<223> OTHER INFORMATION: qPCR Primer

<400> SEQUENCE: 6

```
acttcaattt actatgtagc aaagg                                            25

<210> SEQ ID NO 7
<211> LENGTH: 17
<212> TYPE: DNA
<213> ORGANISM: Artificial Sequence
<220> FEATURE:
<223> OTHER INFORMATION: qPCR Primer

<400> SEQUENCE: 7
gtaaaacgac ggccagt                                                     17

<210> SEQ ID NO 8
<211> LENGTH: 19
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (1)..(1)
<223> OTHER INFORMATION: Hexachloro-fluorescein on 5' end
<220> FEATURE:
<221> NAME/KEY: misc_feature
<222> LOCATION: (19)..(19)
<223> OTHER INFORMATION: Black Hole Quencher on 3' end

<400> SEQUENCE: 8
tactccgacg cggccgcag                                                   19
```

NUCLEIC ACID DETECTION AND QUANTIFICATION

CROSS-REFERENCE TO RELATED APPLICATIONS

This application is a U.S. national phase application of International Application No. PCT/EP2014/077064, filed Dec. 9, 2014, and which claims the benefit of priority of EP Application No. 13196721.8, filed Dec. 11, 2013. The contents of these earlier filed application are hereby incorporated by reference herein in its entirety.

The present invention relates to novel methods and kits and uses to be employed for the detection and/or quantification of one or more target nucleic acid molecules during nucleic acid synthesis.

FIELD OF THE INVENTION

The present invention relates to the field of molecular biology, more particularly to the generation and/or quantification of nucleic acids, and, specifically, to quantitative real-time polymerase chain reaction methods.

BACKGROUND OF THE INVENTION

Quantitative real-time polymerase chain reaction, also abbreviated with qPCR, represents a sensitive method for nucleic acid detection and quantification. It is widely used in basic and biomedical research, in vivo diagnostics, and applied testing.

For one or more specific sequences in a DNA sample, quantitative PCR enables both detection and quantification. The quantity can be either an absolute number of copies or a relative amount when normalized to DNA input or additional normalizing genes. The procedure follows the general principle of polymerase chain reaction; its key feature is that unlike in standard PCR, where the PCR product is detected at the end of the PCR, the amplified DNA is detected as the reaction progresses in "real time".

Generally, two methods for the detection of products in quantitative PCR are employed today, i.e. intercalation of double-stranded DNA-binding dyes on the one hand, and, on the other hand, the use of probes labeled with fluorescent dyes.

Intercalating dyes specific for double-stranded nucleic acids show an increased fluorescence upon intercalating with the double-stranded nucleic acids; as a consequence, the more double-stranded nucleic acid molecules are generated during nucleic acid amplification, the higher gets the increase in fluorescence. Thus, by using intercalating dyes real-time detection of the synthesis of double-stranded PCR products is enabled, and this method allows the initial DNA concentration to be determined with reference to a standard sample. However, and as a consequence, this method also has the drawback that there is no discrimination between correct products and non-specific products such as primer dimers. Also, this method cannot be used to compare levels of different targets. The specificity of the PCR products can be determined by subjecting double-stranded PCR products to incrementally increased temperature to form characteristic dissociation, or melting, curves. With melting curve analysis, the formation of primer dimers and non-specific products can be visualized to monitor qPCR performance.

On the other hand, the second method, i.e. the probe-based detection/Quantification, uses sequence specific DNA-based fluorescence reporter probes, which recognize additional specific sequences within the same PCR amplicon. Sequence specific probes result in quantification of the sequence of interest only and not all ds DNA. The probes contain a fluorescent reporter, such as fluorescein, rhodamine and cyanine, and a quencher to prevent fluorescence. The fluorescent reporter and the quencher are located in close proximity to each other in order for the quencher to prevent fluorescence. Once the probe locates and hybridizes to the complementary target, the reporter and quencher are separated. The means by which they are separated varies depending on the type of probe used. Upon separation, quenching is relieved and a fluorescent signal is generated. The signal is then measured to quantitate the amount of DNA. However, this method, i.e. probe-based qPCR alone, on the other hand, does not give information on whether additional sequences are amplified in the same PCR. Furthermore, in case of suboptimal PCR performance, it is difficult to determine whether PCR failure is caused by inhibitors or conditions leading to formation on non-specific products/primer dimers.

Thus, there still is a need for improved qPCR methods which allow overcoming the above mentioned drawbacks of the methods known in the art.

In view of the above, it is an object of the present invention to provide for tools by means of quantification of a specific target and the total amount of a mixed nucleic acid population can be reliably quantified, and which, in addition, provides for additional advantageous appliances.

The present invention satisfies these and other needs.

SUMMARY OF THE INVENTION

The present invention provides for methods and kits for Method for the detection or quantification of newly-synthesized double-stranded target nucleic acid molecules in a sample during quantitative real-time polymerase chain reaction (qPCR) amplification, the method comprising the steps of (i) contacting a sample comprising one or more target nucleic acid molecules with a) an intercalating dye recognizing double-stranded DNA molecules with higher affinity than single-stranded DNA molecules and said intercalating dye has increasing fluorescence upon intercalation with double-stranded nucleic acid molecules; and with b) at least one fluorophore-labeled oligonucleotide-probe being sequence specific for the target nucleic acid molecule, and said at least one fluorophore-labeled oligonucleotide-probe undergoes a detectable change in fluorescence upon amplification of said one or more target nucleic acid molecules; and with c) unlabeled oligonucleotide-primers being sequence specific for the target nucleic acid molecule; (ii) incubating the mixture of step (i) with a DNA polymerase under conditions sufficient to amplify one or more target nucleic acid molecules; and (iii) detecting the presence or absence or quantifying the amount of the amplified target double-stranded nucleic acid molecules by measuring fluorescence of said intercalating dye and of said fluorophore.

The present invention also relates to the use of a combination of at least one intercalating dye and at least one sequence-specific fluorophore-labeled oligonucleotide-probe in the quantification of specific target and/or total amount of a nucleic acid mixture, or in the determination the cause of suboptimal PCR performance.

The present invention also relates to kits comprising a combination of at least one intercalating dye, and at least one sequence-specific fluorophore-labeled oligonucleotide probe.

Presently, and as generally understood in the state of the art, the term "amplicon" shall mean a piece of DNA or RNA that is the source and/or product of natural or artificial amplification or replication events and can be formed, e.g., by polymerase chain reactions (PCR). In this context, "amplification" refers to the production of one or more copies of a genetic fragment or target sequence, specifically the amplicon. As the product of an amplification reaction, the expression "amplicon" is used interchangeably with the term PCR product.

Presently, and as generally understood, the terms "nucleic acid," "polynucleotide," "oligonucleotide" or "oligo" mean polymers of nucleotide monomers or analogs thereof, including double- and single-stranded deoxyribonucleotides, and ribonucleotides. Usually, the monomers are linked by phosphodiester linkages. Accordingly, the term "nucleotide" refers to organic molecules that serve as the monomers, or subunits, of nucleic acids like DNA and RNA. The building blocks of nucleic acids, nucleotides are composed of a nitrogenous base, a five-carbon sugar (ribose or deoxyribose), and at least one phosphate group.

As used herein, the terms "hybridization" and "hybridizing" refer to the pairing of two complementary single-stranded nucleic acid molecules (RNA and/or DNA) to give a double-stranded molecule. As used herein, two nucleic acid molecules may be hybridized, although the base pairing is not necessarily completely complementary. Accordingly, mismatched bases do not prevent hybridization of two nucleic acid molecules provided that appropriate conditions, well known in the art, are used.

Also herein, the term "primer" refers to a synthetic or biologically produced single-stranded oligonucleotide that is extended by covalent bonding of nucleotide monomers during amplification or polymerization of a (target) nucleic acid molecule. Nucleic acid amplification often is based on nucleic acid synthesis by a nucleic acid polymerase or reverse transcriptase which regularly requires the presence of a primer that may be extended to initiate such nucleic acid synthesis.

Accordingly, the term "probe" as used herein refers to synthetic or biologically produced nucleic acids (DNA or RNA) which, by design or selection, contain specific nucleotide sequences that allow them to hybridize, under defined stringencies, specifically (i.e., preferentially) to target nucleic acid sequences, however, without serving as primers.

The expression "real-time" refers to a method where data collection occurs through periodic monitoring during the course of the amplification/polymerization reaction, thereby combining amplification and detection into a single step.

Also, the term "complementary" refers to the ability of polynucleotides to form base pairs with one another, which are typically formed by hydrogen bonds between nucleotide units in antiparallel polynucleotide strands or regions.

The expressions "target molecule" or "target nucleic acid" or "target sequence" as used herein, are interchangeable and refer to a double-stranded or single-stranded nucleic acid molecule to which a particular primer or probe is capable of preferentially hybridizing and which is to be amplified. In the case of a double-stranded DNA molecule, denaturation of its strands to form a first and a second strand is performed to amplify these molecules. A primer, complementary to a portion of a template is hybridized under appropriate conditions and a DNA polymerase may then synthesize a nucleic acid molecule complementary to said template or a portion thereof.

Further, the terms "fluorophore" or "fluorescent label" and "fluorescent molecule" are interchangeable and refer to a molecule, label or moiety that absorbs energy from light and emits energy as light of a characteristic wavelength. Accordingly, the term "quencher" refers to a molecule, moiety, or label that is capable of quenching a fluorophore emission. This can occur as a result of the formation of a non-fluorescent complex between the fluorophore and the quencher.

Also, herein and as generally understood, the expression "dual-labeled probe" means a single-stranded oligonucleotide labeled with two different dyes, a "reporter" dye, or fluorescent reporter, which is generally located at the 5' end, and a quencher molecule, generally located at the 3' end. The quencher molecule inhibits the natural fluorescence emission of the reporter dye.

Accordingly, a "change in the fluorescence" shall mean either an increase or decrease of fluorescence intensity of the reporter.

Presently, an "intercalating dye recognizing . . . " is to be understood as a colored substance or colourant that has an affinity to a substrate to which it is being applied and that is able to generate fluorescence. Accordingly, the term a "intercalating dye specifically recognizing double-stranded DNA molecules" or "DNA hybrids" as used herein is intended to mean a colored substance being able to a) specifically intercalates with/to DNA/DNA hybrids and b) generate fluorescence upon intercalation, wherein the term "intercalating" with a double stranded DNA molecule (or DNA:DNA hybrid) as used herein is intended to mean the (reversible) inclusion of the dye between the two DNA strands.

Presently, and as generally understood, the "intercalating dye recognizing double-stranded DNA molecules with higher affinity than single-stranded DNA molecules" shall mean that the dye to be employed can also bind to, e.g., single-stranded DNA to some extend but, however, binds with a higher affinity to DNA:DNA hybrids and shows higher fluorescence if bound to DNA:DNA hybrids compared to if bound to single-stranded DNA (or RNA) molecules alone. Accordingly, "intercalating dye recognizing double-stranded DNA molecules" is intended to mean a colored substance being able to a) bind to DNA/DNA hybrids and b) generate fluorescence upon binding thereupon, and "with higher affinity than single-stranded DNA molecules" shall mean that the intercalating dye to be employed binds to and forms a complex with DNA/DNA hybrids with a greater intermolecular force compared to the dye's binding to a single-stranded DNA molecule.

With the methods, uses and kits provided herein, or rather with the combined use of fluorophore-labeled sequence-specific probe and intercalating dye information on the whole PCR as well as on specific amplicons can be gained simultaneously. This is achieved by simultaneously employing the fluorophore-labeled sequence-specific probe and the intercalating dye.

The method can be used to quantify a specific target and total amount of a nucleic acid mixture, and can also be used to determine the cause of suboptimal PCR performance in order to optimize PCR chemistry and the PCR conditions accordingly. The methods, uses and kits provided therein, thus, represent a convenient tool for characterizing DNA libraries, as well as for optimization and screening of nucleic acid amplification assays, chemistry and enzymes.

Accordingly, the method according to the invention can be used in, but not limited to, the following applications: 1) quantifying and qualifying a sequencing library with the same qPCR reaction; 2) optimizing PCR efficiency; 3)

normalizing the amount of the specific species of the nucleic acid to the total nucleic acid population.

Presently, and as generally understood in the relevant field, a "library" is to be understood to mean is a collection of DNA fragments such as cDNA libraries, which are formed from reverse-transcribed RNA, genomic libraries, which are formed from genomic DNA and which represent the entire genome of a given organism, randomized mutant libraries (formed by de novo gene synthesis where alternative nucleotides or codons are incorporated).

Generally, the DNA generation of a library for sequencing involves the addition of defined sequences, i.e. "adapters", which are added at the ends of randomly fragmented DNA. Accordingly, a "sequencing library" represents such a DNA preparation with common or universal nucleic acid ends. The addition of adapters is required to define the site at which the sequencing reactions are to start.

The quality of sequencing data, in particular with next-generation sequencing, depends highly upon the quality of the sequenced library material. Also, since the preparation of high quality libraries at high yield is a critical first step in particular in the next generation sequencing workflow, the present invention provides for an excellent tool in assessing sequencing libraries.

According to a preferred embodiment of the method according to the invention, the intercalating dye can be selected from, but not limited to, SYBR® Green (N',N'-dimethyl-N-[4-[(E)-(3-methyl-1,3-benzothiazol-2-ylidene) methyl]-1-phenylquinolin-1-ium-2-yl]-N-propylpropane-1, 3-diamine), PICOGREEN® (2-(n-bis-(3-dimethylaminopropyl)-amino)-4-(2,3-dihydro-3-methyl-(benzo-1,3-thiazol-2-yl)-methylidene)-1-phenyl-quinolinium), YOYO-1, ethidium bromide.

Numerous intercalating dyes have been developed to be suitable for quantitative real-time PCR (see, e.g., Gudnason et al., Nucleic Acids Res. 2007 October; 35(19):e127) and any of these well-known dyes can be used in the present invention. In a preferred embodiment, SYBR® Green I (N',N'-dimethyl-N-[4-[(E)-(3-methyl-1,3-benzothiazol-2-ylidene)methyl]-1-phenylquinolin-1-ium-2-yl]-N-propyl-propane-1,3-diamine) is used. SYBR® green (N',N'-dimethyl-N-[4-[(E)-(3-methyl-1,3-benzothiazol-2-ylidene) methyl]-1-phenylquinolin-1-ium-2-yl]-N-propylpropane-1, 3-diamine) is available, e.g., from Life Technologies (Invitrogen, USA).

According to another preferred embodiment of the method according to the invention, the fluorophore-labeled oligonucleotide-probe comprises a reporter fluorophore and a quencher fluorophore, the reporter fluorophore being selected from the group consisting of fluorescein, Hexachloro-fluorescein (HEX), 5-carboxyfluorescein (FAM), 4',5'-dichloro-2',7'-dimethoxy-5(6)-carboxyfluorescein (JOE), rhodamine, 6-carboxyrhodamine (R6G), Alexa dyes, CAL Fluor dyes, Quasar dyes, cyanine dyes such as Cy®3 and Cy5, and wherein the quencher fluorophore is being selected from the group consisting of dark quenchers, e.g. a BLACK HOLE QUENCHER® (BHQ), DABCYL (Molecular Beacons), IOWA BLACK® dark quenchers, ECLIPSE® dark quencher; and of fluorescent quenchers, e.g. TAMRA™ (Tetramethylrhodamine).

As mentioned above, according to the invention, the amplified sequences are detected using oligonucleotide probes labeled with both a reporter fluorescent dye at one end and a quencher of fluorescence at the opposite end of the probe. The close proximity of the reporter to the quencher prevents detection of its fluorescence. Breaking the reporter-quencher proximity allows emission of fluorescence which can be detected after excitation with a light source.

Suitable fluorophore-labeled probes are, e.g. TaqMan® probes, molecular beacons, Scorpio, or hybridization probes, which all make use of reporter-quencher fluorophores: TaqMan® probes (Roche Molecular Systems, Inc.) are dual labeled hydrolysis probes consisting of a 18-22 bp oligonucleotide probe which is labeled with a reporter fluorophore at the 5' end and a quencher fluorophore at the 3' end. With the probes, the 5' exonuclease activity of the enzyme Taq Polymerase is used for measuring the amount of target sequences in the PCR reaction: As long as the probe is not hydrolyzed, the quencher and the fluorophore remain in proximity to each other, separated only by the length of the probe, whereby the fluorescence of the reporter is prevented by the quencher. During PCR, the oligonucleotide probe specifically anneals between the forward and reverse primer to an internal region of the amplicon. The DNA polymerase extends the sequence-specific primer with the incorporation of nucleotides that are complementary to the DNA template. The 5' exonuclease activity of the DNA polymerase then cleaves the probe thus displacing the reporter molecule from the close vicinity of the quencher resulting in fluorescence. The fluorescence accumulates as cycling of PCR continues and is measured at the end of each PCR cycle. The intensity of fluorescence generated by the Reporter molecule above background level (i.e. the "Ct value" (cycle threshold)) is measured and used to quantitate the amount of newly generated double-stranded DNA strands.

The method of any of the preceding claims, wherein the sample further contains a reverse transcriptase.

This embodiment implies that the method according to invention can also be applied in quantification reactions where a reverse transcriptase is present in the reaction mixture, be it due to a reverse transcription reaction performed prior to the quantitative real-time polymerase chain reaction, or be it to study the impact/characteristics of reverse transcriptase on the qPCR reaction.

Reverse transcriptase can bind to DNA templates with high affinity and in turn inhibit PCR. RT can also cause non-specific primer extension in a PCR reaction mix a lower temperature and lead to the formation of primer dimer and/or non-specific PCR products, both of which negatively affect one-step- and two-step RT-PCR reactions, leading to lower PCR efficiency and sensitivity. With the method according to the invention, i.e. with the combined use of the intercalating dye and the fluorophore-probe, it is possible to differentiate between those tow different mechanisms.

According to a preferred embodiment, the detection is performed using a spectrophotometric real-time PCR instrument. Such an instrument is a machine that amplifies and detects DNA and combines the functions of a thermal cycler and a fluorimeter, enabling the process of quantitative PCR. A real-time PCR instrument monitors the progress of PCR, and the nature of amplified products, by measuring fluorescence. By using an instrument with sufficient optical channels and extensive assay optimization, several separate targets can be simultaneously quantified in a single PCR reaction. Known and suitable instruments are, e.g. available from Qiagen, Hilden, Germany (e.g. the Rotorgene series).

Accordingly, the target nucleic acid to be quantified or detected can be selected from the group consisting of DNA and cDNA. The targets may be produced (for example cDNA) or can be found in biological samples. The biological sample may be used without treatment or the biological samples may be treated to remove substances that may interfere with the methods disclosed herein.

The target nucleic acid may be human or animal, or of microorganisms, etc., and may, e.g. be human genomic DNA.

According to a preferred embodiment of the method according to the invention, the target nucleic acid is a specific target in a mixed nucleic acid sample and the method is used to quantify the specific target nucleic acid in the mixture and the total amount of nucleic acid mixture simultaneously.

According to another preferred embodiment of the method according to the invention, the target nucleic acid is a group of nucleic acids with a common sequence (e.g. an adaptor sequence) that are present in a mixed nucleic acid sample with and without this common sequence. Also, the method is used to quantify the specific group of target nucleic acids in the mixture and the total amount of nucleic acid mixture simultaneously.

According to a preferred embodiment, the oligonucleotide-primer pair is selected from a common primer pair recognizing adaptors or a sequence-specific oligonucleotide-primer pair.

Polymerases used in accordance with the invention may be any enzyme that can synthesize a nucleic acid molecule from a nucleic acid template, typically in the 5' to 3' direction.

According to a preferred embodiment of the method, the uses and the kits according to the invention, the polymerase is selected from the group consisting of a taq polymerase, KlenTaq, TopTaq polymerase, Tfi, Pfu, KOD, Therminator.

As mentioned above, the taq polymerase has 5' exonuclease activity; like any other polymerase it extends the sequence-specific primer with the incorporation of nucleotides that are complementary to the DNA template, while the taq polymerase's 5' exonuclease activity then cleaves the probe, thus displacing the reporter molecule from the close vicinity of the quencher resulting in fluorescence. The taq polymerase has also the advantage that it is thermostable the fact of which enables running the qPCR at high temperature, which facilitates high specificity of the primers and reduces the production of unspecific products. Moreover, use of the thermostable polymerase eliminates the need for having to add new enzyme to the PCR reaction during the thermocycling process.

As mentioned above, the invention also relates to the use of a combination of a) an intercalating dye recognizing double-stranded DNA molecules with higher affinity than single-stranded DNA molecules and said intercalating dye has increasing fluorescence upon intercalation with double-stranded nucleic acid molecules, and of b) at least one fluorophore-labeled oligonucleotide-probe being sequence specific for the target nucleic acid molecule, and said at least one fluorophore-labeled oligonucleotide-probe undergoes a detectable change in fluorescence upon amplification of said one or more target nucleic acid molecules, in a quantitative real time polymerase chain reaction.

In the use according to the invention, the same preferred embodiments apply as mentioned above for the method according to the invention.

According to one aspect of the use and the method according to the invention, the combination is used for quantifying one or more specific target nucleic acids and the total amount of a nucleic acid mixture containing the specific target nucleic acids simultaneously. Thus, the method using the combination may be used, e.g. to study splicing isoforms, metagenomics, and DNA/RNA libraries.

E.g., a duplex PCR can be performed, specifically amplifying two certain genes, such as 18 S RNA and GAPDH (Glyceraldehyde 3-phosphate dehydrogenase) from human genomic DNA; the total amount of both genes are quantified by the intercalating dye while that of one gene can be specifically quantified with the sequence-specific fluorophore-labeled oligonucleotide-probe.

Also, the use and the method according to the invention can be employed for, e.g., DNA library quantification and qualification: the total library can be amplified with a common primer pair recognizing adaptor sequences and quantified based on the intercalating dye signal. In the same reaction, one or more specific genes or sequences can be amplified with either the same common primer pair or a different, sequence-specific primer pair, and quantified with a sequence-specific fluorescence-labeled probe or probes. The quantity of the specific sequences present in the whole library can act as an indicator of the library preparation efficiency and control for potential bias introduced during library preparation.

Also, the present invention relates to the use according to the invention for determining the cause of suboptimal polymerase chain reaction performance. As already described for the method according to the invention, with the use of the combination of intercalating dye and sequence-specific fluorophore-labeled oligonucleotide probe it can be differentiated whether a suboptimal PCR reaction is due to inhibition through an interfering enzyme such as reverse transcriptase, or due to nonspecific primer extension and formation of primer dimer and/or non-specific PCR products.

Accordingly, the present invention relates to a kit for the quantification or detection of one or more target nucleic acid molecules in a sample during nucleic acid synthesis, comprising (a) a DNA polymerase; (b) an intercalating dye recognizing double-stranded DNA molecules with higher affinity than single-stranded DNA molecules and said intercalating dye has increasing fluorescence upon intercalation with double-stranded nucleic acid molecules; and (c) at least one fluorophore-labeled oligonucleotide-probe being sequence specific for a target nucleic acid molecule, and said at least one fluorophore-labeled oligonucleotide-probe undergoes a detectable change in fluorescence upon amplification of said one or more target nucleic acid molecules.

It is particularly preferred if the DNA polymerase is selected from the group comprising a taq polymerase, KlenTaq, and TopTaq.

According to another preferred embodiment, the intercalating dye is selected from SYBR® Green (N',N'-dimethyl-N-[4-[(E)-(3-methyl-1,3-benzothiazol-2-ylidene)methyl]-1-phenylquinolin-1-ium-2-yl]-N-propylpropane-1,3-diamine), PICOGREEN® (2-(n-bis-(3-dimethylaminopropyl)-amino)-4-(2,3-dihydro-3-methyl-(benzo-1,3-thiazol-2-yl)-methylidene)-1-phenyl-quinolinium), YOYO-1, ethidium bromide.

Also, in a preferred kit of the invention, the reporter fluorophore is selected from fluorescein, Hexachloro-fluorescein (HEX), 5-carboxyfluorescein (FAM), 27'-dimethoxy-4'5'-dichloro-6-carboxyfluorescein (JOE), rhodamine, 6-carboxyrhodamine (R6G), N,N,N',N'-tetramethyl-6-carboxyrhodamine (TAMRA™), 6-carboxy-X-rhodamine (ROX), 4-(4'-dimethylaminophenylazo) benzoic acid (DABCYL), and 5-(2'-ami-noethyl)aminonaphthalene-1-sulfonic acid (EDANS), Alexa dyes, CAL Fluor dyes, Quasar dyes, cyanine dyes such as Cy®3 and Cy5, and wherein the quencher fluorophore is being selected from the group consisting of a BLACK HOLE QUENCHER® (BHQ), TAMRA™, DABCYL dark quenchers, IOWA BLACK® dark quenchers, and an ECLIPSE® Dark quencher.

With the kits according to the invention, a tool is provided to perform the methods and uses of the invention.

Unless defined otherwise, all technical and scientific terms used herein generally have the same meaning as commonly understood by one of ordinary skill in the art to which this invention belongs.

Further advantages follow from the description of the embodiments and the attached drawings.

It goes without saying that the abovementioned features and the features which are still to be explained below can be used not only in the respectively specified combinations, but also in other combinations or on their own, without departing from the scope of the present invention.

Figure 1B:
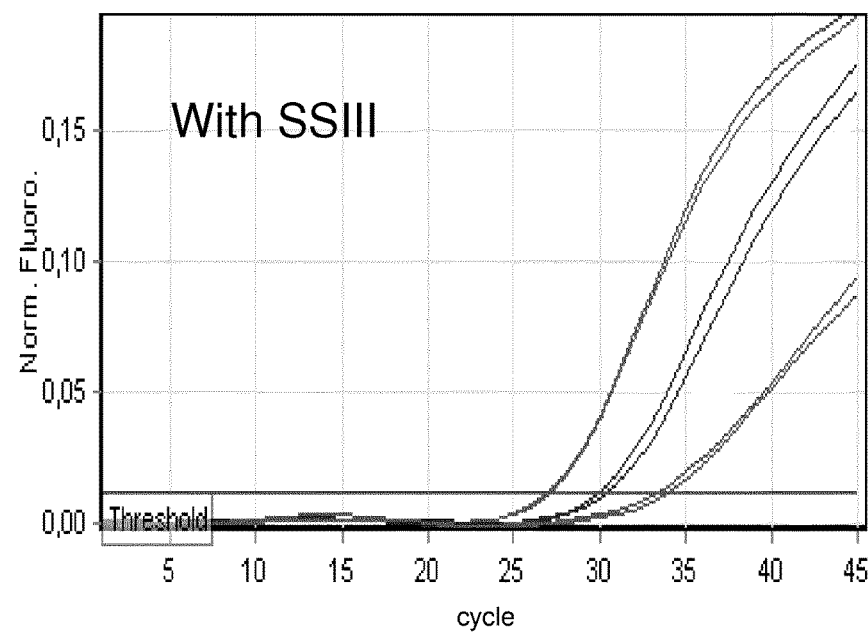
Figure 2A:
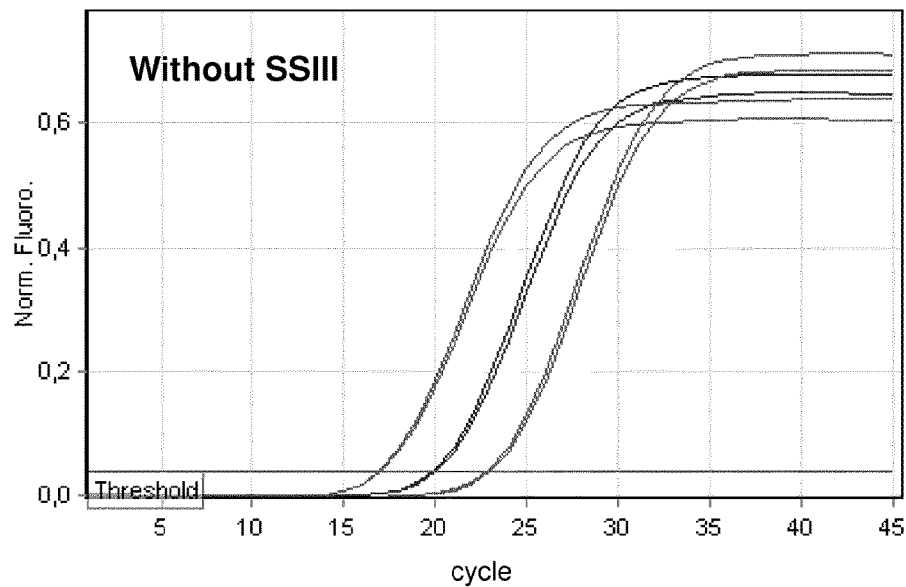
Figure 2B:
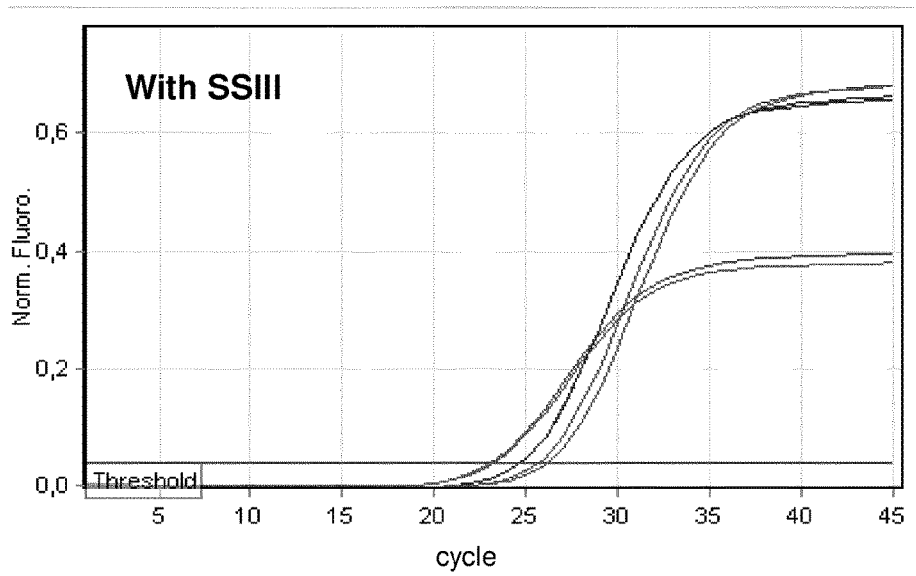
Figure 3A:
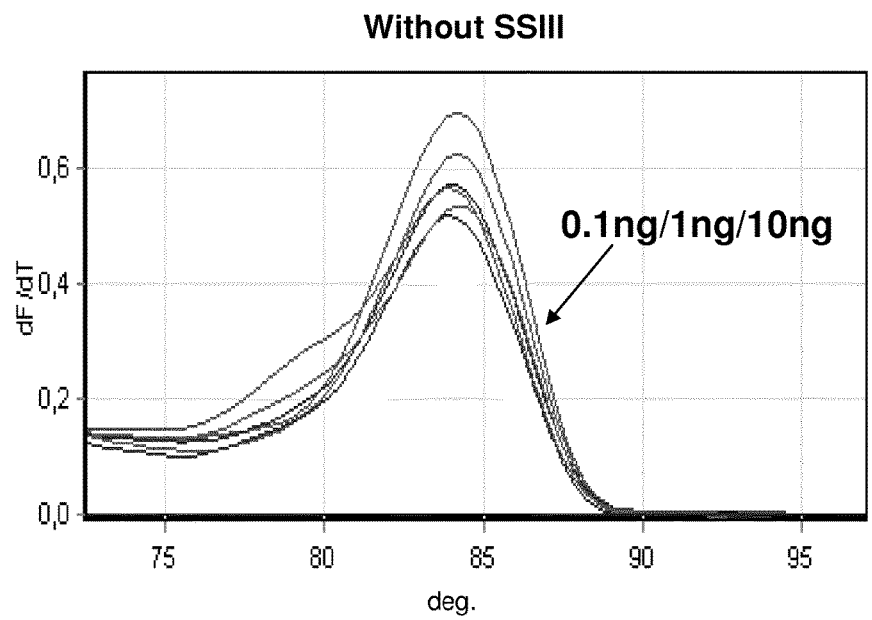
Figure 3B:
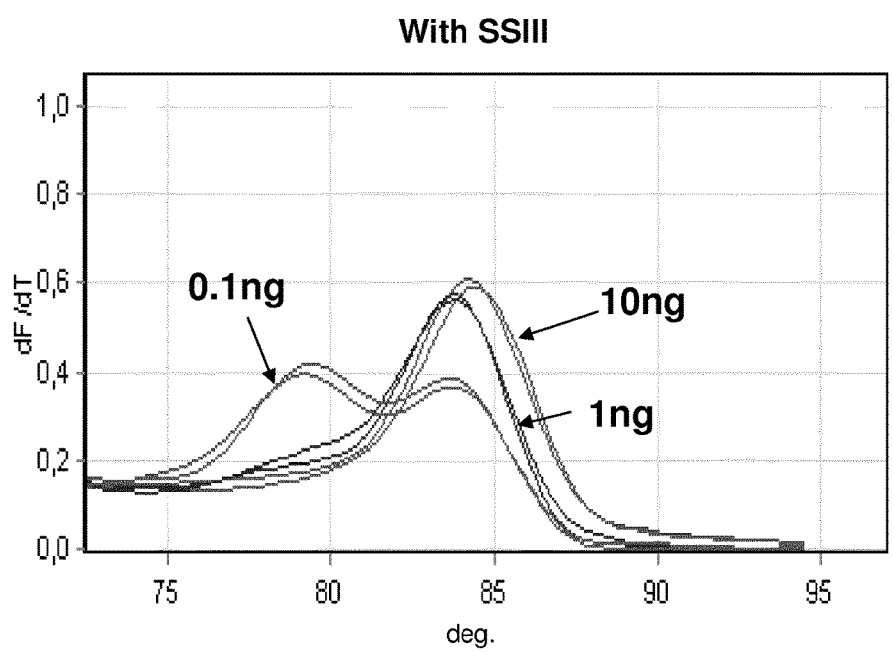
Figure 4A:
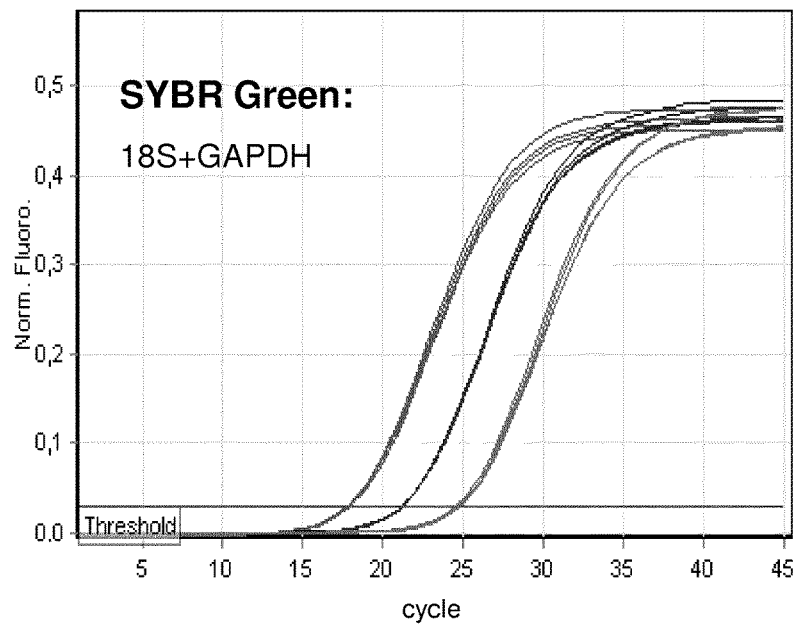
Figure 4B:
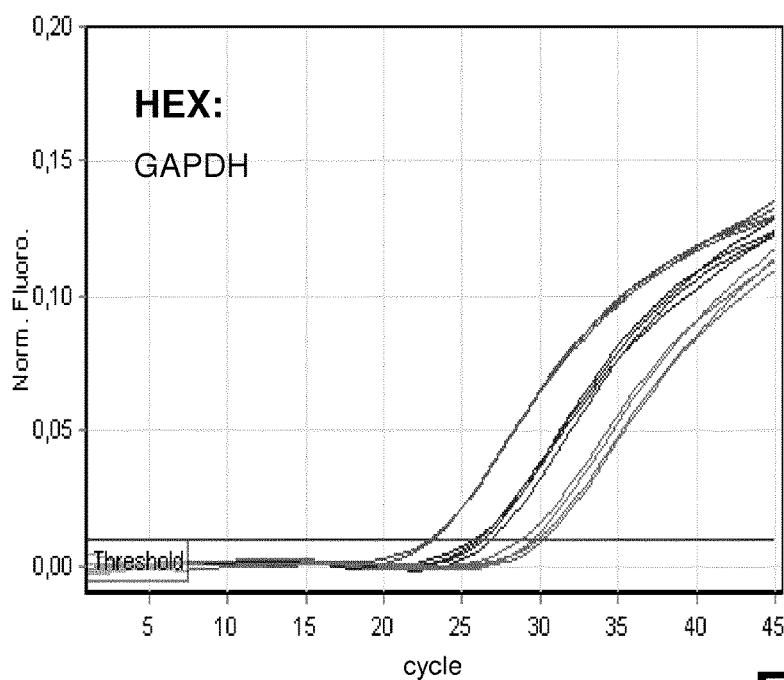
Figure 5:
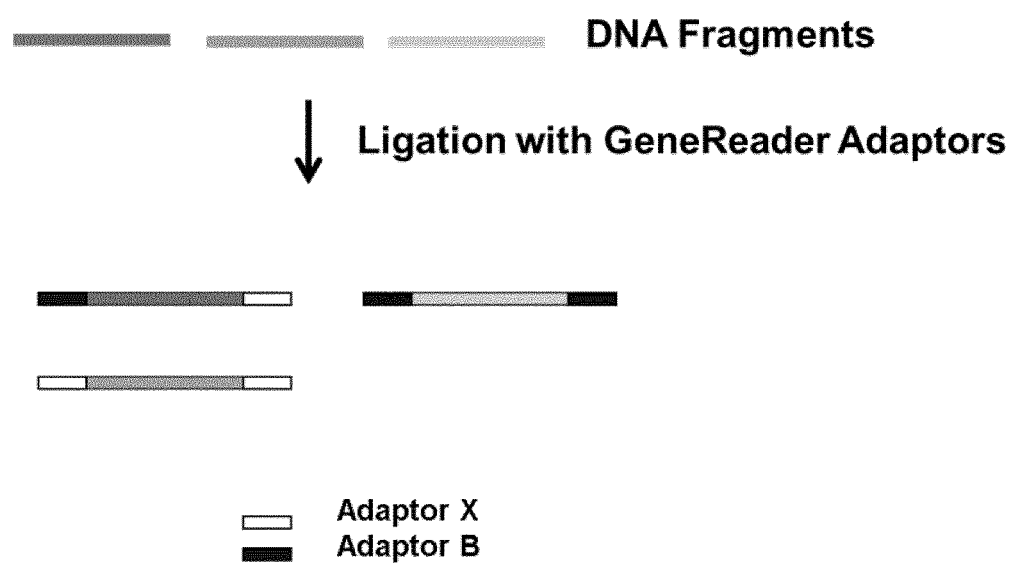
Figure 6A:
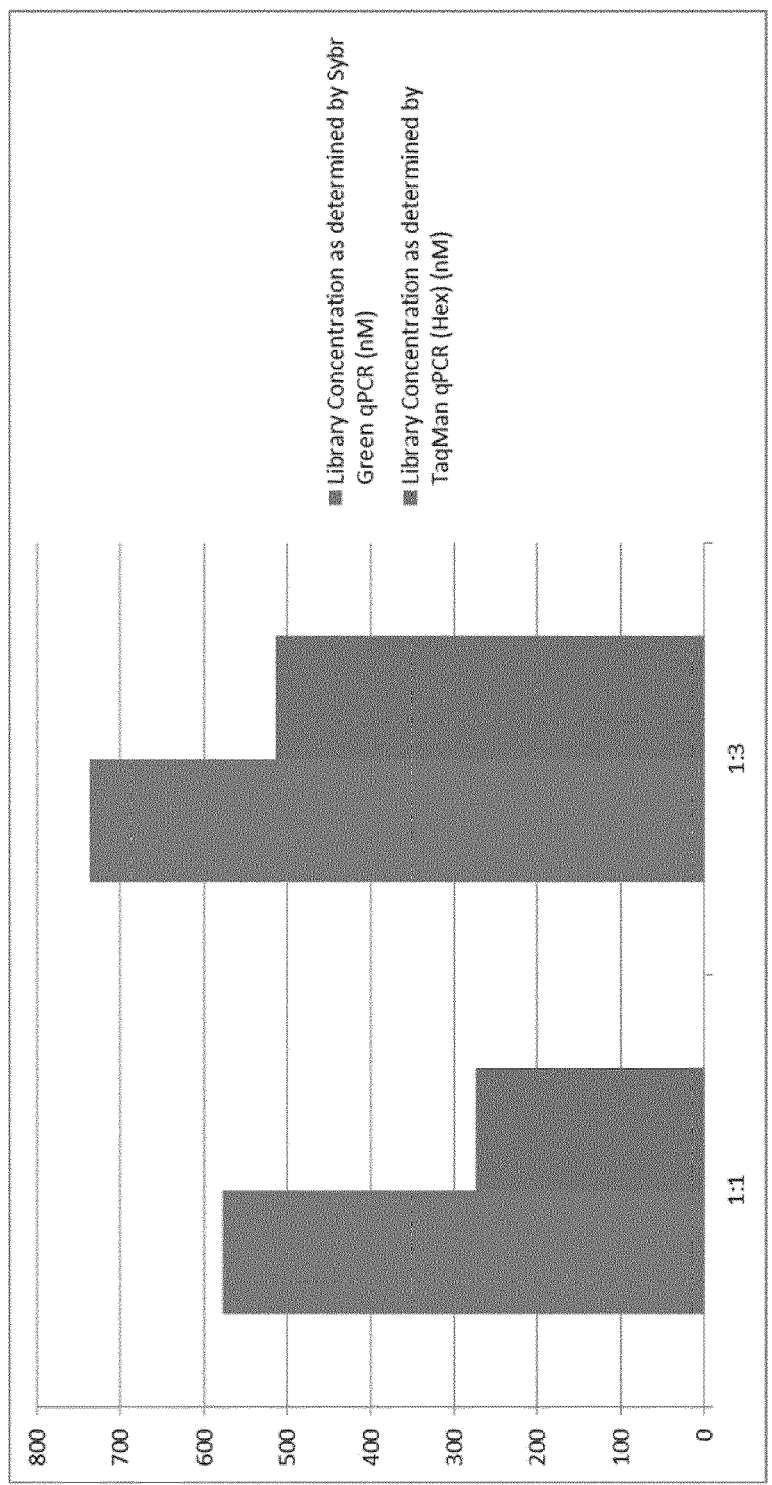

Several embodiments of the invention are illustrated in the figures and explained in more detail in the following description. In the figures:

FIG. 1 shows the results of an experiment using the method according to the invention for determining the exact causes of suboptimal qPCR: FIGS. 1A and 1 B shows amplification plots and FIGS. 1 C and 1 D show tables summarizing the mean Ct values in the HEX-channel of the qPCR reactions for the specific amplification of the GAPDH gene. The qPCR reactions were performed in the presence of SYBR® Green with specific primers and HEX-labeled TaqMan probe that recognize GAPDH gene. Different amounts of human genomic DNA (0.1 ng, 1 ng, and 10 ng) were used as template. RT enzyme SUPERSCRIPT® III (SSI 11) was either absent (FIG. 1 A, 1 C) or present (1 OOU/reaction, FIG. 1 B, 1 D) in the qPCR. Both amplification plots (FIG. 1A, FIG. 1 B) and mean Ct values in the HEX-channel (FIG. 1 C, FIG. 1 D) are shown here to demonstrate compromised PCR performance caused by SUPERSCRIPT® III (later Ct values, lower fluorescence signals);

FIG. 2 shows the results for the SYBR Green signals of the qPCR reaction of FIG. 1, with amplification plots in FIGS. 2A and 2B, and with a table displaying the mean Ct values (FIGS. 2C and 2D); the results demonstrate compromised PCR performance caused by SuperScript III, i.e. later Ct values, lower fluorescence signals;

FIG. 3 shows the results of close examination of the melting curves of the qPCR products of the same experiment as in FIGS. 1 and 2, which products were subjected to dissociation with temperature gradually rising from 72° C. to 95° C. directly after PCR; the melting curves from PCR reactions with SuperScript III are shown in FIG. 3A and those from PCR reactions without SuperScript III are shown in FIG. 3B;

FIG. 4 shows the results for another experiment using the method according to the invention, where simultaneous quantification of the total amount of a mixed nucleic acid population and a specific target sequence in the population was performed; FIG. 4A demonstrates the quantification of both GAPDH and 18s amplicons with SYBR Green amplification plots; FIG. 4B demonstrates specific quantification of GAPDH gene through HEX amplification plots; FIG. 4C is a summary of mean Ct values of qPCR on both SYBR Green and HEX channels;

FIG. 5 shows a schematic diagram of a workflow for constructing a sequencing library, in particular for the GeneReader sequencer (QIAGEN), wherein Adaptor B is the adaptor that has binding site for the sequencing primer; and FIG. 6. shows the results of another experiment using the method according to the invention, where a sequencing library as generated according to FIG. 5 was used, and where a simultaneous quantification of the total amount of a mixed nucleic acid population and a specific target sequence in the population was performed: FIG. 6A shows a diagram displaying the results of the determination of the library concentration via SYBR Green qPCR (nM; left columns, respectively) and via TaqMan qPCR (nM; right columns, respectively); the table in FIG. 6B summarizes these results.

EXAMPLES

Example 1

With the method and uses according to the present invention, the causes of suboptimal PCR performance can be assessed with the aim to optimize the PCR chemistry and the PCR conditions accordingly.

Thus, in a first experiment, it was assessed which impact the enzyme reverse transcriptase—which is often present in PCR reaction due to prior reverse transcription reactions that are performed in the same vessel as a subsequent PCR reaction—has on the qPCR reaction.

Reverse transcriptase can inhibit PCR through its binding to DNA templates, and it can also cause nonspecific primer extension in a PCR reaction mix and lead to the formation of primer dimer and/or non-specific PCR products. Both mechanisms can negatively affect one-step and two-step reverse transcriptase PCR reactions, leading to lower PCR efficiency and sensitivity. In order to be able to differentiate between those two different mechanisms, the method according to the invention was applied:

In the performed experiment, the impact of reverse transcriptase SUPERSCRIPT® III (Life Technologies, Invitrogen, USA) on the specific qPCR amplification of the GAPDH (Glyceraldehyde 3-phosphate dehydrogenase) gene was assessed: All qPCR reactions in the examples were performed on Rotorgene Q (QIAGEN, Hilden Germany). Each 25 µl qPCR reaction contained as final concentrations 1×HotStar Taq Mastermix and additional MgCl2 to give 2.5 mM final concentration (all from QIAGEN), and 0.2× SYBR® Green (LIFE Technologies, Invitrogen, USA). Two sequence specific oligonucleotide-primers (TTCCAC-CCATGGCAAAT (SEQ ID NO: 1) and GAAGATGGT-GATGGGATTTC (SEQ ID NO:2)), each at a final concentration of 0.4 µM, and one HEX-labeled TaqMan probe (HEX-CAA GCT TCC CGT TCT CAG CC-BHQ (SEQ ID NO: 3) with a final concentration of 0.2 µM, were used in qPCR to amplify and detect human GAPDH gene from 0.1 ng, 1 ng, and 10 ng human genomic DNA, respectively.

To examine the effects on PCR efficiency, 100 U of SuperScript III Reverse Transcriptase (LIFE Technologies) were added to the qPCR reaction mixture. All qPCR reactions were performed in triplicates with the following cycling protocol: 95° C., 15 min for initial denaturation; followed by 45 cycles of 95° C., 30 seconds and 60° C., 1 minutes. Fluorescence signals were collected at 60° C. in both Green and Yellow channels.

The results of this experiment are shown in FIG. 1 The enzyme SuperScript III (SSIII) was either absent (FIG. 1A, 1C) or present (100 U/reaction, FIG. 1B, 1D) in the qPCR. The amplification plots are shown in FIGS. 1A and 1B, the mean Ct values in the HEX-channel in FIGS. 1C and 1D.

As shown in FIG. 1, the qPCR inhibition by SuperScript III was evidenced by later Ct values in yellow channel, which represent signals generated by the HEX-labeled TaqMan probe that specifically recognizes GAPDH sequence. This was also reflected by the change of shape and Ct values of the SYBR Green amplification curves that were detected on Green channel (see FIG. 2). However, with amplification curves alone, it is not possible to determine whether the less efficient PCR amplification is caused by direct inhibition or RT-induced non-specific amplification.

A close examination of the melting curve in the green channel (FIG. 3) suggested that the later Ct value with 1 ng and 10 ng DNA as template was mainly caused by inhibition, not non-specific amplification, as shown by the single melting peak. In contrast, an additional melting peak appears at lower temperature in the PCR products with 0.1 ng DNA as template, suggesting that both inhibition and non-specific amplification could account for the late Ct value in this case.

With the above employed and described method according to the invention compromised PCR performance caused by SuperScript III (later Ct values, lower fluorescence signals) could be demonstrated.

Example 2

In another experiment, the method according to the invention was used to quantify a specific target in a mixed nucleic acid population and the total amount of nucleic acid mixture simultaneously. Accordingly, the method according to the invention may be used for quantification and qualification of, e.g., a DNA library.

For this purpose, a duplex PCR experiment was performed where both 18s (Primers: GCCGCTAGAGGT-GAAATTCTTG (SEQ ID NO: 4) and CATTCTTG-GCAAATGCTTTCG (SEQ ID NO: 5)) and GAPDH genes (Primers: TTCCACCCATGGCAAAT (SEQ ID NO: 1) and GAAGATGGTGATGGGATTTC (SEQ ID NO: 2)) were amplified from human genomic DNA and the total amount of both genes were quantified by SYBR® Green while that of the GAPDH was specifically quantified by using HEX-labeled TaqMan probe HEX-CAA GCT TCC CGT TCT CAG CC-BHQ (SEQ ID NO: 3).

FIG. 4A demonstrates the quantification of both GAPDH and 18s amplicons with SYBR Green amplification plots, while FIG. 4B demonstrates specific quantification of the GAPDH gene through HEX amplification plots. FIG. 4C is a summary of mean Ct values of qPCR on both SYBR Green and HEX channels, giving PCR efficiency of 103.5% and 97.6%, respectively.

As shown in FIG. 4, quantitation with both SYBR Green and HEX-labeled TaqMan probe gave good PCR efficiency and linearity with a range of 0.1 ng to 10 ng template DNA.

Thus, the method according to the invention can be easily adapted for the quantification and qualification of DNA library for various sequencing methods including high-throughput sequencing. E.g., for quantification and qualification of the high-throughput sequencing library, the total library can be amplified with a common primer pair recognizing adaptor sequences and quantified based on SYBR Green signal. In the same reaction, a specific gene or sequence, or several specific genes/sequences can be amplified with either the same common primer pair or a different, sequence-specific primer pair, and quantified with a sequence-specific fluorescence-labeled probe or probes.

The quantity of the specific sequences present in the whole library can act as an indicator of the library preparation efficiency and control for potential bias introduced during library preparation Example 3

In yet another experiment, the method according to the invention was used to simultaneously quantify a specific target in a mixed nucleic acid population and the total amount of nucleic acid mixture.

FIG. 5 shows a diagram displaying the construction flow for generating a library for use, e.g., in a sequencer such as the GeneReader (QIAGEN): For this purpose, DNA fragments, generated either by random fragmentation, enzymatic fragmentation, or PCR, were ligated with platform-specific adaptors B and X in order for them to be clonally amplified and then sequenced. As a consequence, there were three possible combinations of the adaptors after ligation: (i) the DNA fragment will be ligated with the X adaptor at one end and the B adaptor at the other end; (ii) the DNA fragment will be ligated with two B adaptors at both ends; and (iii) the DNA fragment will be ligated with two X adaptors at both ends. Since the B adaptor is the adaptor that has binding site for the sequencing primer, only B adaptor-containing library fragments ('effective libraries') were sequenced on the sequencer, e.g. the GeneReader, platform in that way.

It could be shown that different ratios of the X and B adaptors in the ligation reaction (X:B=1:1 or 1:3) can lead to different percentages of the effective library in the total library, as determined by the dual-color qPCR reaction method described herein (see FIG. 6). PhiX174 RF1 genomic DNA (Thermoscientifc, Cat # SD0031) was randomly fragmented on the Corvaris focused-ultrasonicators and then constructed into sequencing library with GeneReader Library Construction Kit according to manufacturer's instruction (Qiagen) with the following deviation: at the combined ligation and nick translation step, X adaptor and B adaptor were added either in the ratio of 1:1, or 1:3. The GeneReader libraries were then quantified with the dual-color qPCR method described in this invention. PCR Primers are: Primer B: 5' ACT TCA ATT TAC TAT GTA GCA AAG G 3' (SEQ ID NO: 6); Primer X: 5'-GTA AAA CGA CGG CCA GT 3' (SEQ ID NO: 7). TaqMan Probe is: B2 HEX: 5' HEX T ACT CCG ACG CGG CCG CAG BHQ 3' (SEQ ID NO: 8). QuantiFast Sybr Green PCR Mix (Qiagen) was used for the qPCR quantification according to the manufacturer's instruction, with the deviation that 0.2 µM final concentration of the B2 HEX TaqMan probe was added to the qPCR reaction.

From FIG. 6 it can be taken that absolute qPCR Quantification was used to quantify the library, with a plasmid containing B adaptor and X adaptor flanking a 307 bp DNA fragment as quantification standard. The total amount of library with all three possible combinations of the adaptors B and X (see FIG. 5) was determined by the absolute Sybr Green qPCR; while the amount of the libraries that contain B adaptor was determined by the TaqMan qPCR quantification where B2 HEX TaqMan probe was used. As shown in FIG. 6A and FIG. 6B, higher ratio of B:X adaptor in the ligation reaction generated higher ratio of B-adaptor-containing effective libraries (B:X=1:1, effective library percentage is 47.23%; while with B:X of 3:1, effective library percentage is 69.61%).

The dual-color qPCR method described in the invention therefore conveniently quantified the total ligation product amount, as well as the amount of the effective library, simultaneously in the same qPCR reaction. The results indicated that higher B adaptor ratio increases percentage of the effective library and therefore library construction efficiency.

Accordingly, the method according to the invention was used for quantification and qualification of a DNA library and accurately determination of the amount of effective library (or, sequencable library) in the total adaptor ligation product. Therefore this method can also be used to optimize library construction conditions with the aim to increase percentage of the effective library in the total adaptor ligation product.

The invention claimed is:

1. A method comprising
   a) ligating adaptors to DNA fragments to produce a population of library adaptor ligation products
   b) combining the population of library adaptor ligation products with
      i.) an intercalating dye recognizing double-stranded DNA molecules with higher affinity than single-stranded DNA molecules and said intercalating dye has increasing fluorescence upon intercalation with double-stranded nucleic acid molecules, and
      ii.) at least one fluorophore-labeled oligonucleotide-probe being sequence specific for one or more target nucleic acid molecules, and said at least one fluorophore-labeled oligonucleotide-probe undergoes a detectable change in fluorescence upon amplification of the one or more target nucleic acid molecules, in a quantitative real time polymerase chain reaction;
   c) incubating the mixture of step (b) with a DNA polymerase under conditions sufficient to amplify one or more of the population of library adaptor ligation products, wherein amplification results in a sequencing library comprising one or more amplified library adaptor ligation products;
   d) detecting the presence or absence or quantifying the amount of the amplified one or more sequencing library adaptor ligation products by measuring fluorescence of said intercalating dye and of said fluorophore; and
   e) determining, based on the fluorescence of intercalating dye and fluorophore detected in step d), the percentage of effective sequencing library in the total population of library adaptor ligation products and the efficiency of sequencing library construction or determining the percentage of effective sequencing library in the total population of library adaptor ligation products and simultaneously determining the quantity and quality of the sequencing library.

2. The method of claim 1, wherein the intercalating dye is selected from N',N'-dimethyl-N-[4-[(E)-(3-methyl-1,3-benzothiazol-2-ylidene)methyl]-1-phenylquinolin-1-ium-2-yl]-N-propylpropane-1,3-diamine, (2-(n-bis-(3-dimethylaminopropyl)-amino)-4-(2,3-dihydro-3-methyl-(benzo-1,3-thiazol-2-yl)-methylidene)-1-phenyl-quinolinium), {1,1'-(4,4,8,8-tetramethyl-4,8-diazaundecamethylene)bis[4-[(3-methylbenzo-1,3-oxazol-2-yl)methylidene]-1,4-dihydroquinolinium] tetraiodide}, ethidium bromide.

3. The method of claim 1, wherein the fluorophore-labeled oligonucleotide-probe comprises a reporter fluorophore and a quencher fluorophore, the reporter fluorophore being selected from the group consisting of fluorescein, Hexachloro-fluorescein (HEX), 5-carboxyfluorescein (FAM), 2'7'-dimethoxy-4'5'-dichloro-6-car-boxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), and 5-(2'-aminoethyl)aminonaphthalene-1-sulfonic acid (EDANS), Alexa dyes, CAL Fluor dyes, Quasar dyes, cyanine dyes, and wherein the quencher fluorophore is a dark quencher or fluorescent quencher.

4. The method of claim 1, wherein the detection is performed using a spectrophotometric real-time PCR instrument.

5. The method of claim 1, wherein the oligonucleotide-primer pair is selected from a common primer pair recognizing adaptors or a sequence-specific oligonucleotide-primer pair.

6. The method of claim 1, wherein the DNA polymerase is selected from the group consisting of a Taq, Tfi, KOD, PFu, or their derivatives.

* * * * *